United States Patent
Harter et al.

(10) Patent No.: US 6,318,203 B1
(45) Date of Patent: Nov. 20, 2001

(54) DRIVE FOR ROTATING OBJECT SUCH AS A ROLLER, SHAFT, PLATE OR THE LIKE

(75) Inventors: Erich Harter; Alfred Hitzler, both of Mochenwangen (DE)

(73) Assignee: Venta Airwasher LLC., Grove Village, IL (US)

( * ) Notice: Subject to any disclaimer, the term of this patent is extended or adjusted under 35 U.S.C. 154(b) by 0 days.

(21) Appl. No.: 09/222,726

(22) Filed: Dec. 29, 1998

(51) Int. Cl.$^7$ ................................ F16H 1/16; F16H 1/20
(52) U.S. Cl. ............................................................ 74/425
(58) Field of Search .......................... 74/425, 458, 435, 74/457, 47, 48, 116, 117, 126, 128, 129; 261/92; 96/289, 294

(56) References Cited

U.S. PATENT DOCUMENTS

| | | | |
|---|---|---|---|
| 3,738,185 | * | 6/1973 | Wooley .................................. 74/116 |
| 3,765,303 | * | 10/1973 | Fischer et al. ..................... 74/458 X |
| 3,834,680 | * | 9/1974 | Yost et al. ............................... 261/92 |
| 4,261,930 | * | 4/1981 | Walker ............................... 261/92 X |
| 5,090,261 | * | 2/1992 | Nakatsukasa ........................... 74/425 |
| 5,802,921 | * | 9/1998 | Rouverol ............................... 74/458 |
| 5,816,523 | * | 10/1998 | Hori ................................... 74/435 X |

FOREIGN PATENT DOCUMENTS

0838610A2   4/1998 (EP) .

\* cited by examiner

*Primary Examiner*—David A. Bucci
*Assistant Examiner*—Colby Hansen
(74) *Attorney, Agent, or Firm*—Venable; George H. Spencer; Robert Kinberg

(57) ABSTRACT

A drive for rotating an article such as a roller shaft or plate has a gear which is connected to the rotating article in a rotationally fixed manner. The gear has a number of teeth. A means for driving the gear has a movably mounted lever with a tip that meshes with the gear to have driving contact with the gear and impart driving motion to the gear. The tip forms a tooth and the gear teeth and the tooth of the lever tip are shaped to mesh with a rolling contact between them during the driving motion.

16 Claims, 9 Drawing Sheets

DRIVE FOR ROTATING OBJECT SUCH AS A ROLLER, SHAFT, PLATE OR THE LIKE

BACKGROUND OF THE INVENTION

The invention relates to a drive for a rotating article

Such a drive has already been disclosed by European Laid-open Specification EP 083 8610 A2. The main item of this drive is at least one pivotably mounted lever, which interacts with a gear, which is connected to the rotating article in a rotationally fixed manner. To this end, there is a device for mounting and guiding the lever for a driving forward motion, meshing with the gear, of the lever.

This drive has the advantage that it is essentially insensitive to contaminants which occur due to a liquid in which rollers, shafts or the like rotate in an air-humidifying and cleaning unit, a deodorizer or the like. For even if the gear is wetted in the process by the liquid due to the rotational motion in the liquid, the only point of contact with the further components of the mechanism is in that part of the lever which meshes with the gear. However, this part of the lever is simple to clean as a rule.

However, a disadvantage of this mechanism consists in the fact that, in particular due to the occurrence of production tolerances of the drive parts, smooth, quiet running of the rotating article is impaired from time to time, since, in particular, the meshing lever may become stuck with the gear.

SUMMARY OF THE INVENTION

The object of the invention is to provide a drive which has improved synchronism and is in particular less sensitive to production tolerances.

The invention is based on a drive for a rotating article for a roller, shaft, plate or the like, in particular for a deodorizer, an air humidifier or an air-cleaning unit or the like, which has the following features.

A movably mounted lever, a gear which is connected to the rotating article in a rotationally fixed manner, and a lever mechanism means for a driving motion, meshing with the gear, of the lever in order to rotate the gear, are provided with the lever having a tip for meshing with the teeth of the gear. The central idea of the invention, then, is to design the tip in the form of a tooth, the shape of this tooth and that of the teeth of the gear as well as the lever mechanism being matched to one another in such a way that the tooth flanks of the tooth on the at least one lever and the respectively meshing tooth on the gear roll on one another during the driving motion. This measure achieves a situation in which the drive, even when production tolerances occur, sets the gear and the rotating article in a smooth motion, in the course of which sticking of lever tip and gear can be avoided. This is because the configuration according to the invention essentially fulfills the mathematical interrelationships of a conventional tooth system between two gears. In addition, the wear of the tooth flanks in contact is thereby markedly improved compared with the solution from the prior art, since the sliding motion, which is otherwise present, between the flanks is greatly reduced and is essentially replaced by a rolling motion. This has a positive effect, in particular, on the service life of the drive and on the operating noise.

In order to improve the synchronism of the drive still further, it is also proposed that the shape of the tooth on the lever and that of the teeth of the gear as well as the lever mechanism be matched to one another in such a way that the tooth flanks of the tooth on the at least one lever and the respectively meshing tooth on the gear, during the driving motion, have a point of contact at which the flanks roll on one another without radial sliding (rolling point).

The shape of the tooth on the lever and that of the teeth on the gear are preferably designed according to the rules of tooth engagement as an involute, cycloidal or circular arc tooth system or as a lantern tooth system, in which the tooth on the lever has, for example, the shape of a pin. In this way, an essentially constant transmission ratio between lever mechanism and gear can be realized.

In an especially advantageous refinement of the invention, the lever mechanism contains guide surfaces for the lever for the sliding guidance of the lever. As a result, the lever, in a guided manner, can perform, for example, a forward motion, a reverse motion and a pivoting motion. In this connection, it is advantageous if the lever mechanism comprises an eccentric drive for the lever. By the articulation points of the lever and the guide surfaces on the housing of the lever mechanism being geometrically arranged in such a way as to be appropriately matched to one another, a desired coupler curve can be realized for the cyclic meshing of the tooth-shaped tip of the at least one lever. Instead of the operating principle, thereby realized, of the slider-crank mechanism, the operating principle of the inverted slider crank, in which the longitudinal guide is located in the lever, and, for example, a pin secured in the housing of the lever mechanism engages in this longitudinal guide, may also be applied in another embodiment.

Furthermore, to realize a simple eccentric drive, it is proposed that this eccentric drive have a drive shaft for the lever, and this drive shaft is arranged eccentrically on a gear. The gear may be driven continuously, preferably by means of a worm. As a result, extreme transmission ratios are possible on the one hand, which is necessary in particular during use in a deodorizer or air washer according to the invention, where only one motor is used for the direct drive of the fan and the drive of one or two plate stacks. On the other hand, a worm gear unit constitutes a so-called self-locking gear unit, as a result of which the at least one lever is locked against undesirable motion.

In a preferred embodiment, the drive shaft is attached directly and eccentrically to a gear which is driven by a worm.

The worm is preferably connected to the drive shaft of a motor via an elastic coupling. In this way, the drive shaft need not be absolutely exactly in alignment with the worm shaft. In this case, larger tolerances during the production of a drive according to the invention are possible, which, inter alia, brings about a cost saving.

In an especially advantageous refinement of the invention, there are two, three or more levers, which mesh alternately with the gear. As a result, at least one lever is constantly in mesh with the toothed or pin ring of the rotating article, so that the latter is driven smoothly. Furthermore, in the event of the levers being locked by a worm gear unit against an undesirable motion, it is ensured that the rotating article is also secured against any undesirable further motion, for example against turning back, by at least one meshing lever. The rotation of the rotating article is therefore constantly controlled in a mechanically fixed manner by the lever drive.

Furthermore, it is especially preferred if the at least one lever is elastically mounted between the guide surfaces of the lever mechanism. As a result, the lever is prestressed in the lever mechanism and exhibits no play even where there are production tolerances. Excessive play could, in the worst case, lead to the tooth of a meshing lever colliding with a tooth of the gear or to the teeth sticking.

In this case, it is especially preferred if, to elastically mount the lever between the guide surfaces, at least part of the outer contour of the lever gripped by the guide surfaces is elastically resilient. In this connection, it is advantageous if, to realize an elastically resilient outer contour of the lever, the outer contour is designed as a narrow frame. In particular, if the lever is made of plastic, this contour region consequently has elastic properties.

Furthermore, in order to further improve the elastic properties, it is preferred if the frame is interrupted, a spring element being fitted in place at the point of interruption.

Finally, in order to ensure effective force transmission of the at least one lever to the gear, it is proposed that that region of the outer edge of the lever which is supported on a guide surface of the lever mechanism in order to absorb the major force for a further motion of the gear not be elastically resilient.

BRIEF DESCRIPTION OF THE DRAWINGS

Several exemplary embodiments of the invention are shown in the drawings and explained in more detail below with indication of further advantages and details. In the drawing.

DETAILED DESCRIPTION OF THE PREFERRED EMBODIMENTS

Figure 1:
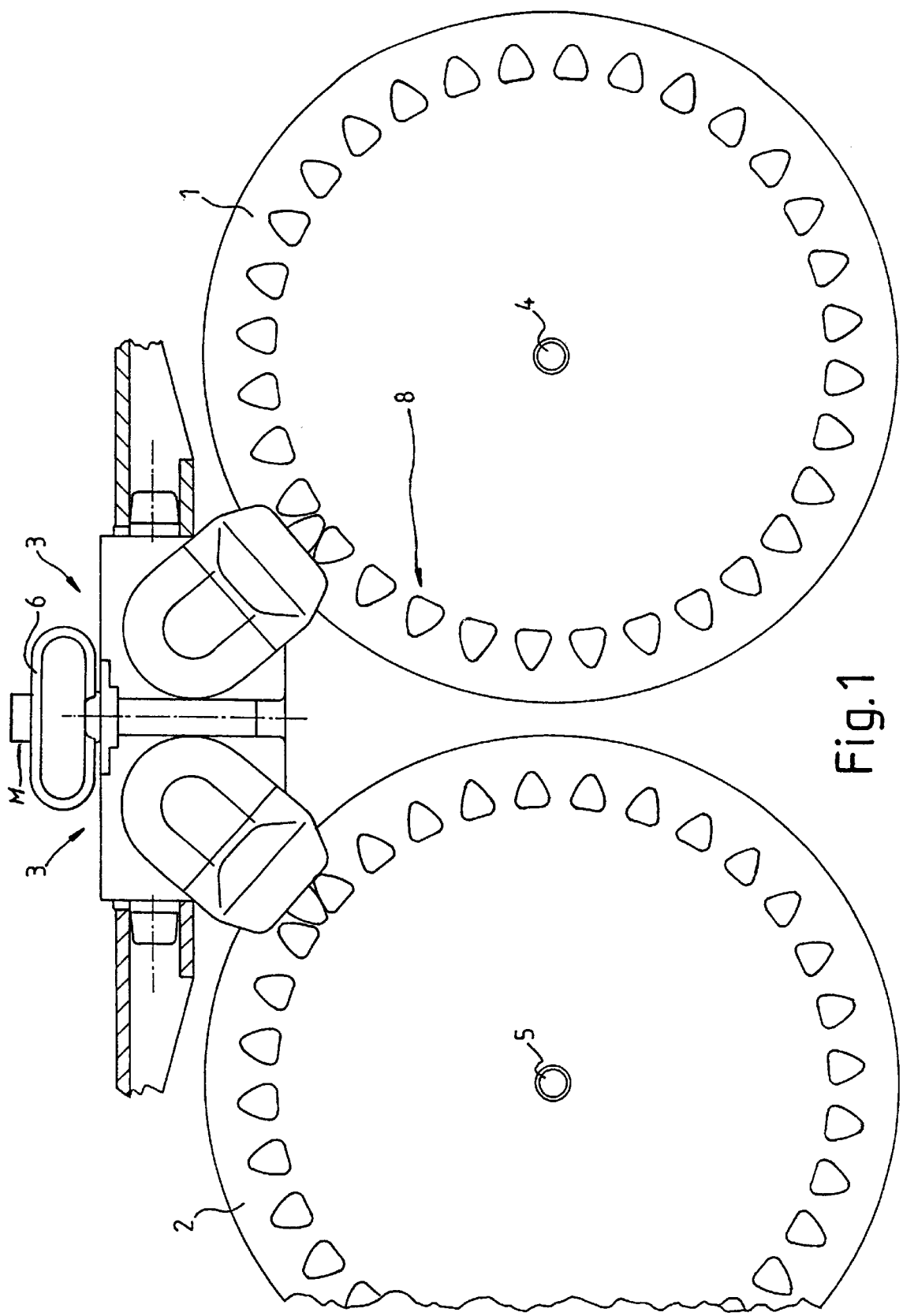
FIG. 1 shows a side view of two plate stacks, arranged next to one another, of an air-humidifying unit with drives according to the invention arranged thereon in each case, in schematic side view.

Two plate stacks 1, 2, mounted in parallel, of an air-humidifying unit with drives 3 according to the invention arranged thereon are shown in FIG. 1 in a schematic side view. The plate stacks 1, 2 consist, for example, of circular disks arranged one behind the other in a lamellar manner. In the air washer, the plate stacks 1, 2 are normally mounted on a trough(not shown), in which water, if need be with an additive, is located as a rule, the plate stacks plunging into the water during a rotation about axes 4, 5. Likewise not shown is a housing cover, on which, for example, a fan with drive motor, which is connected to the two drives 3 according to the invention via an elastic coupling 6, is arranged.

In FIGS. 2a–e, the drive 3 according to the invention is shown as an enlarged detail in sectional view for different lever positions. These figures show a lever mechanism means 7, which interacts with a toothed ring 8, which is arranged on the end face of the plate stack 1. The lever mechanism 7 is an arrangement having two drive levers 9, 10. The drive levers 9, 10 in each case have a tip 11, 12 of tooth-shaped design as well as a location opening 13, 14 (also see FIGS. 3a and b) for two drive journals 15, 16 in each case. The drive journals 15, 16 are attached to the two end faces of a worm wheel 17 in such a way as to be eccentrically offset by 180° and thus form an eccentric bearing seat for the drive levers 9, 10 slipped into position thereon via the location openings 13, 14. The worm wheel 17 has a rotary spindle 18, which is mounted in the housing of the lever mechanism 7 and is in engagement with a worm 19. The worm 19 is connected to, for example, a drive motor M via the elastic coupling 6. When the worm 19 rotates and when the worm wheel 17 rotates as a result, for example in the direction of the arrow, the drive levers 9, 10 are moved or pivoted back and forth in the housing of the lever mechanism 7 via the location openings 13, 14, of the drive levers 9, 10 mounted on the drive. In the process, the outer contour of the drive levers 9, 10 bears against guide surfaces 20, 21 of the housing of the lever mechanism 7.

Figure 2A:
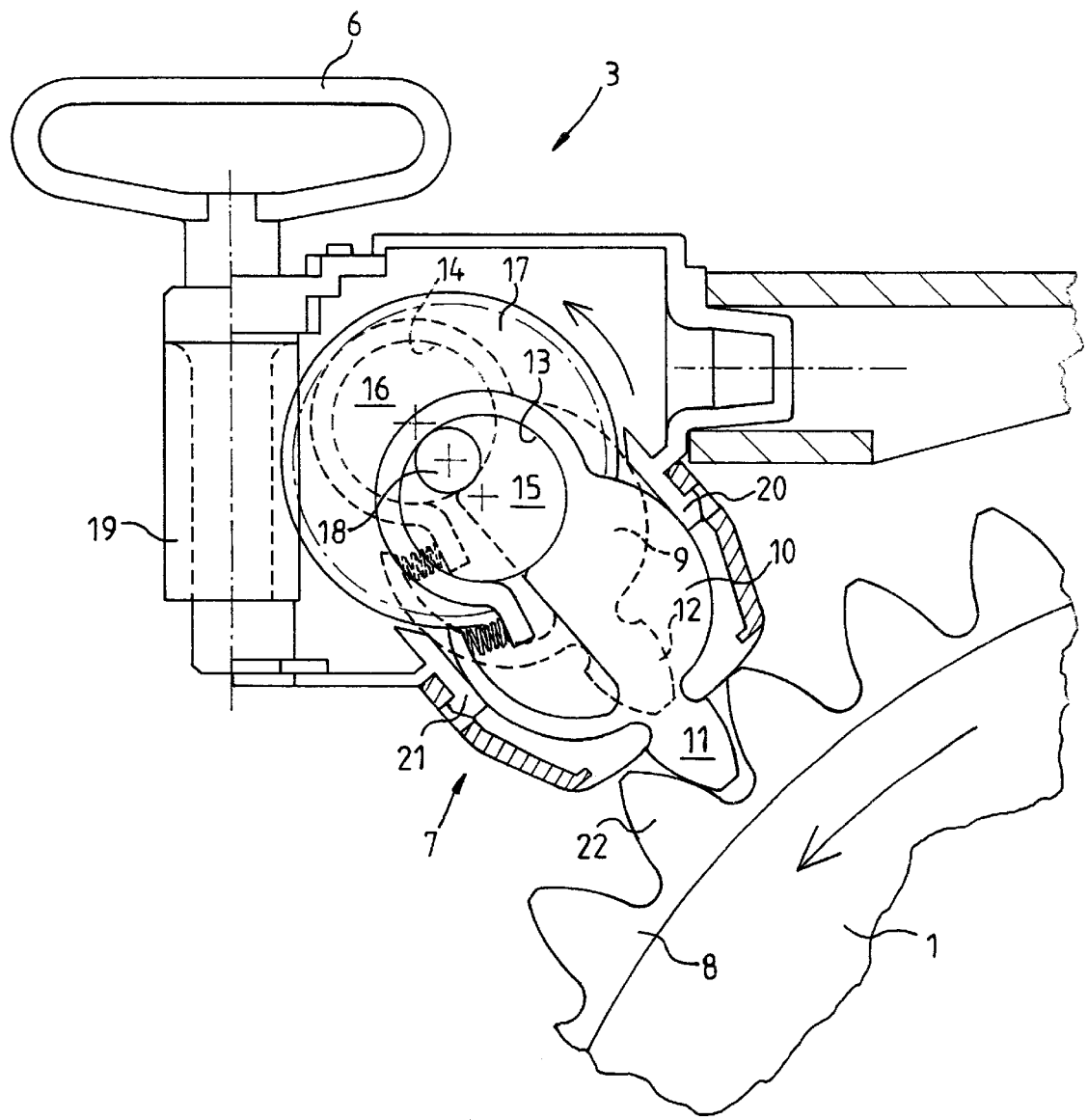
FIGS. 2a–e show a schematic cross-sectional detail of a drive according to the invention in accordance with FIG. 1 for different lever positions.
Figure 2B:
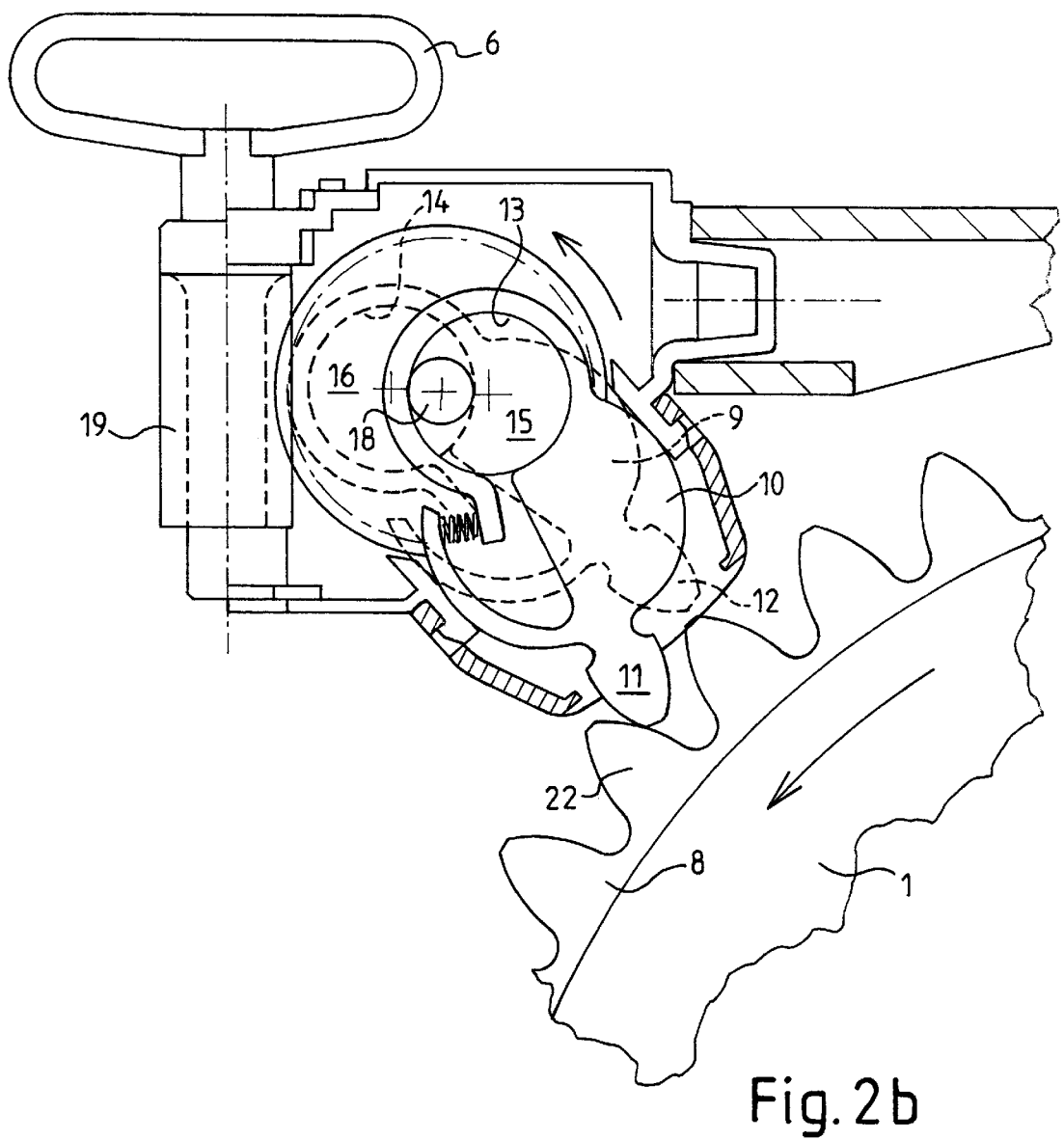
Figure 2C:
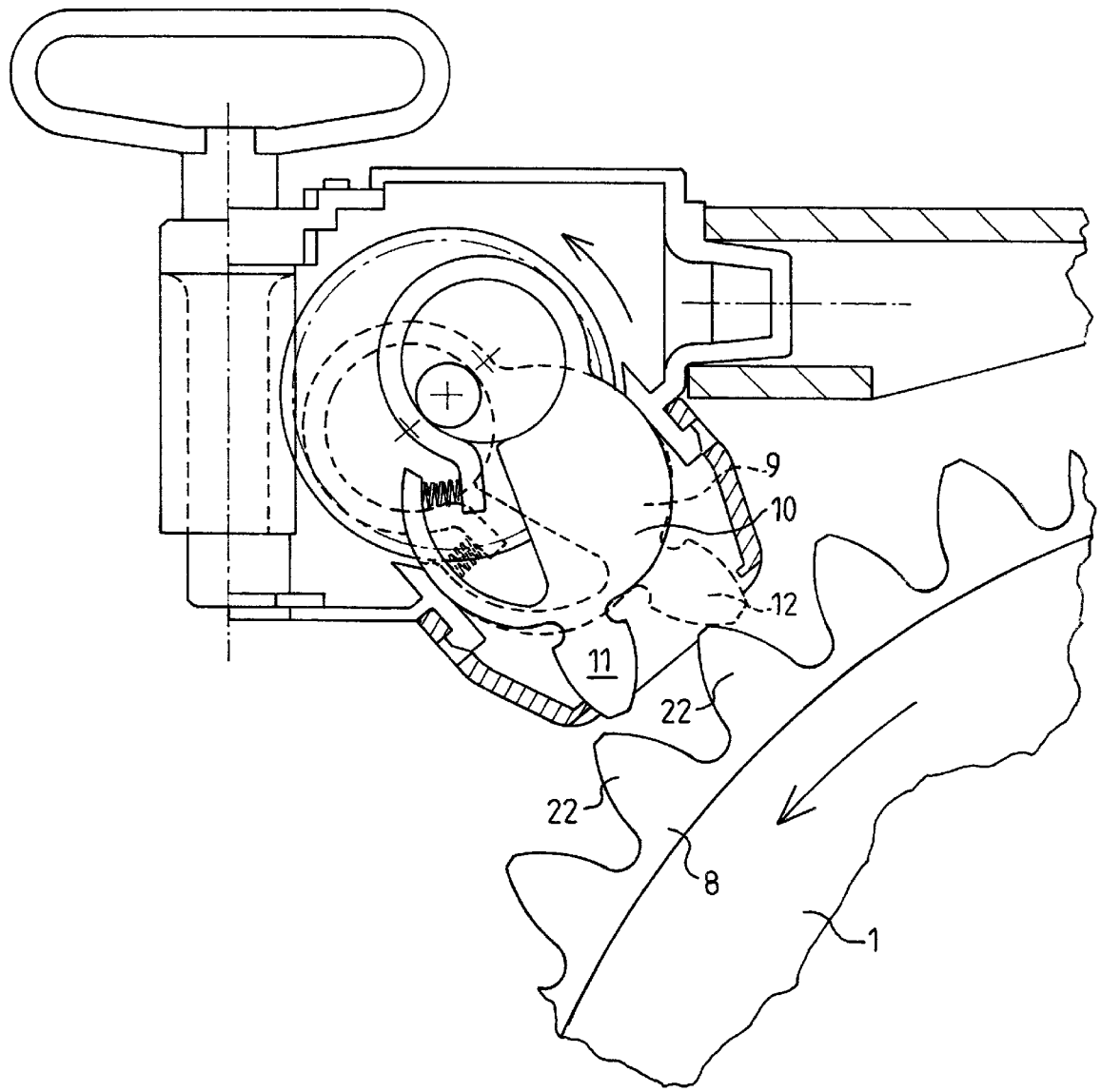
Figure 2D:
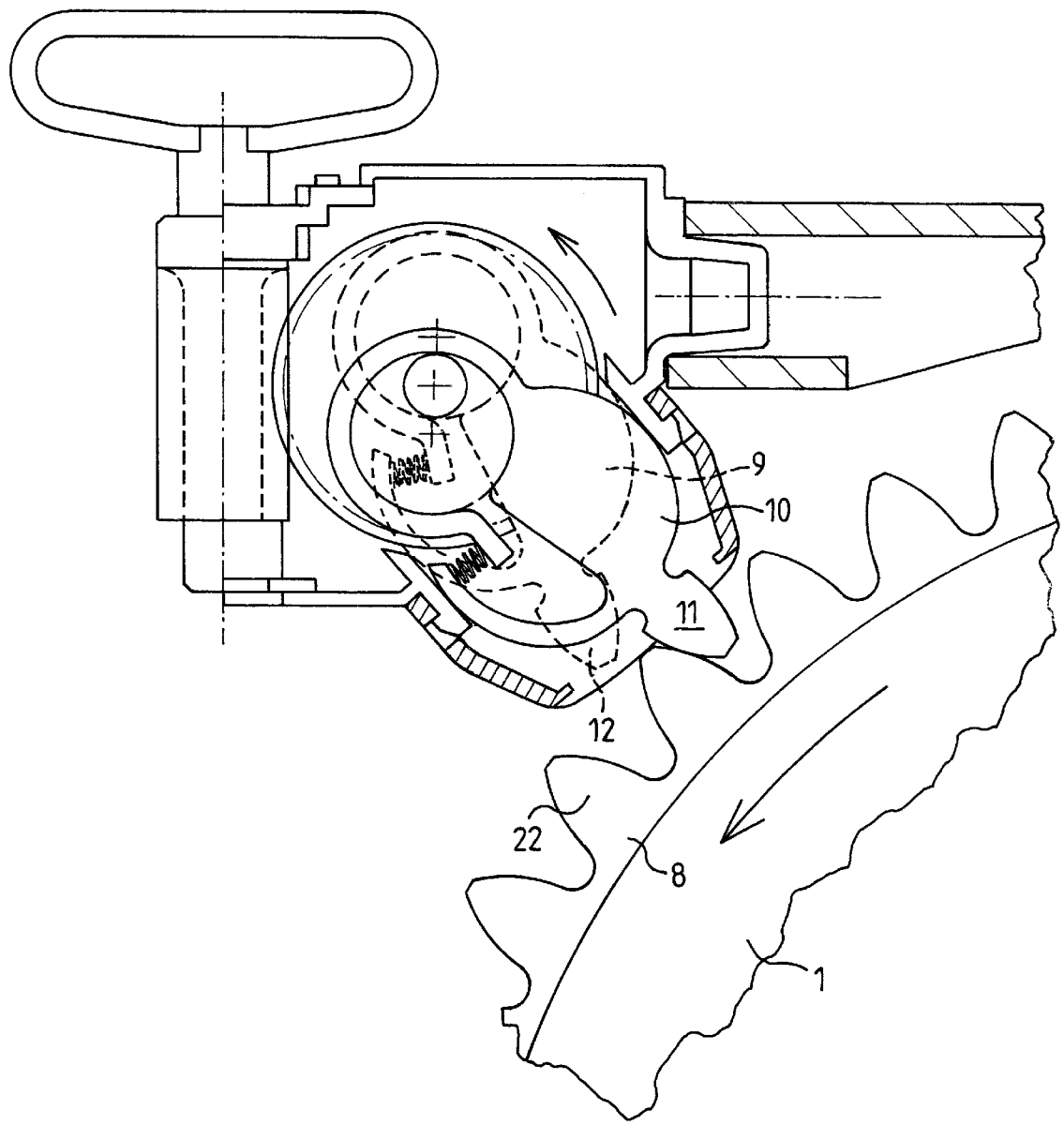

In FIG. 2a, the front drive lever 10 (shown in solid lines) is in mesh with the tooth system of the toothed ring 8, whereas the second drive lever 9 (shown in broken lines) arranged behind it has been completely retracted from the tooth system of the toothed ring 8. The desired motion of the tooth-shaped tips 11, 12 of the drive levers 9, 10 results essentially from the geometric distances between the eccentrically arranged drive journals 15, 16 as well as from the shape and the distance between the guide surfaces 20, 21. The path curve of the tooth-shaped tips 11, 12 appears as a coupler curve of the slider-crank mechanism which is thus realized.

Figure 2E:
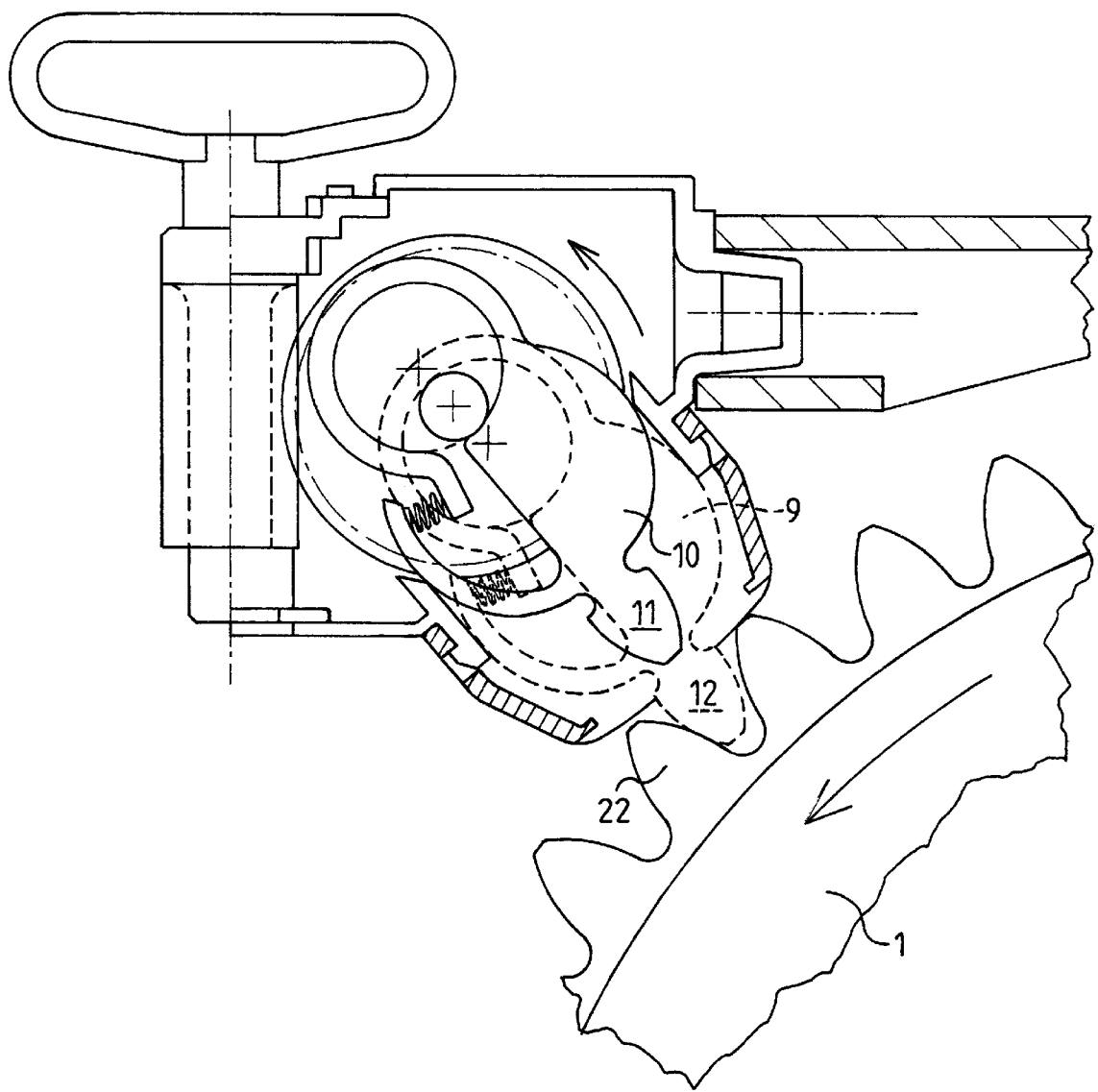

The motion of the drive levers 9, 10 for obtaining a rotary motion of the toothed ring 8, arranged on the plate stack 1, in the direction of the arrow is depicted in different angular positions of the worm wheel 17 in FIGS. 2a to e. Here, each figure corresponds to a state of the lever position for a rotation of the worm wheel 17 through 45°. That is to say, FIG. 2e represents a rotation through 180°, provided FIG. 2a is established at 0°.

The shape of the teeth 22 of the toothed ring 8 and of the tooth-shaped tip 11, 12 is designed in such a way that the intermeshing teeth realize, by way of example, a cycloidal tooth system. In addition, the motion of the drive levers 9, 10 is coordinated by the eccentric mounting and the guide surfaces on the housing of the lever mechanism in such a way that the tooth flanks roll on one another.

Figures 3A, 3B, 3C:
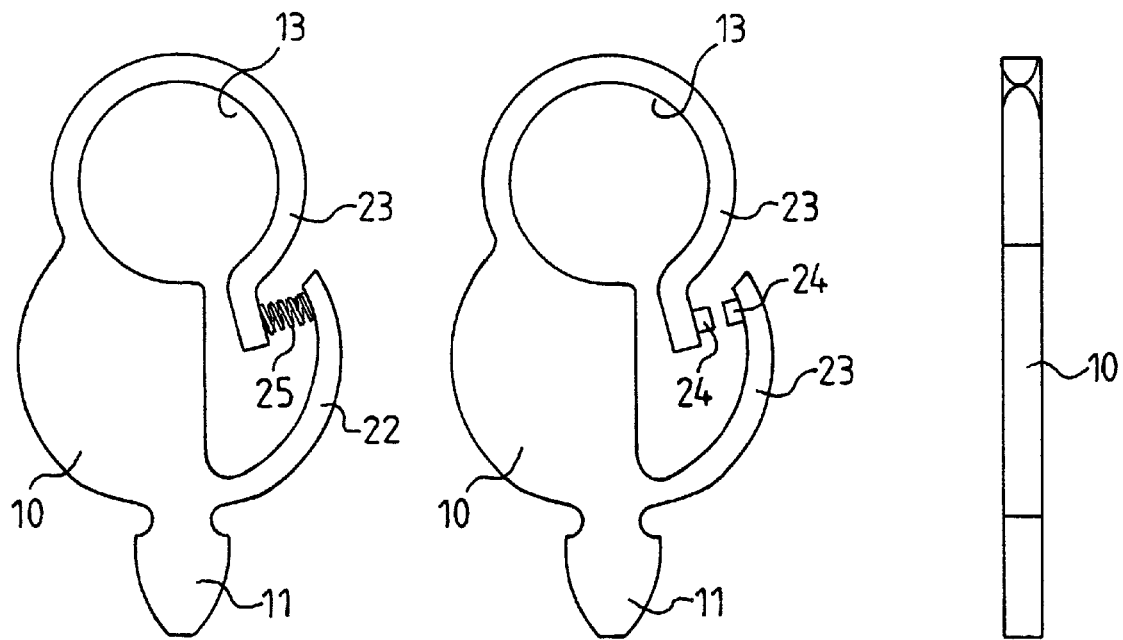
FIGS. 3a–c show a lever according to the invention in two plan views with and without spring element and in a side view.

The drive lever 10 is again shown in detail by way of example in FIGS. 3a to c. The outer contour of the drive lever 10 is designed as a narrow frame 23 over a large region on one side. The frame 23 is interrupted in front of the location opening 13 and has location pins 24 for a compression spring 25 (only shown in FIG. 3a). In this way, the front region of the drive lever 10 is elastically resilient on this side. This enables the drive lever 10 or the drive lever 9 of identical design to be inserted with prestress into the housing of the lever mechanism 7. This prevents the levers 9, 10 from exhibiting play where production tolerances occur, this play possibly leading to the tip 11, 12 of a drive lever 9, 10 colliding with or becoming stuck to a tooth of the toothed ring 8. The asymmetrical frame formation enables the lever to be supported on a guide surface without yielding. This is preferably the side which absorbs the major forces for the further motion of the gear.

Figure 4:
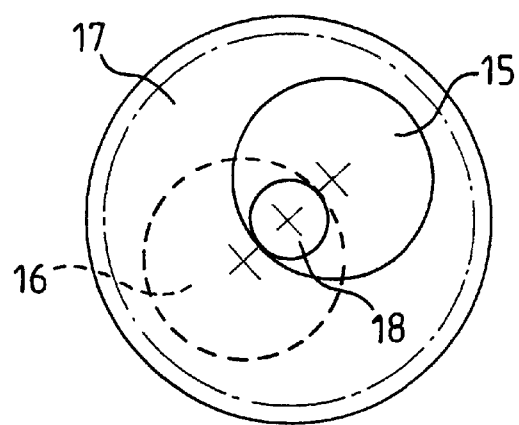
FIG. 4 shows a worm wheel with eccentrically arranged drive shaft for a lever according to FIGS. 3a to c in a schematic plan view.

The worm wheel 17 with the drive journals 15, 16 arranged on both end faces in such a way as to be eccentrically offset by 180° is again shown as a detail in FIG. 4.

As already mentioned above, the mounting of the worm wheel 17 is effected via bearing spindles 18, which project from the eccentrically arranged drive shafts 15, 16.

As can be seen in particular from FIG. 1, the tips 11, 12 of the drive levers 9, 10 are directed downward, so that liquid, which is delivered to the lever tips 11, 12 by the plunging of the toothed ring 8 into a liquid bath, runs off again down to the toothed ring 8. The only locations which can therefore connect with the liquid of the bath are merely the tooth-shaped tips 11, 12 of the drive levers 9, 10. There is therefore no risk of the remaining components of the drive coming into contact with the bath liquid during any operational phase of the unit. For the layman, dismantling the unit for cleaning work is possible in a simple manner, since, with removal of the cover (not shown), only the plate stacks 1, 2 are still located in the trough (not shown).

The drive shown for a plate stack 1, 2 can be used outside an air-humidifying unit according to the invention. The system shown can be readily used on any rotating article with which a drive system according to the invention offers advantages. This may be the case, in particular, in chemical production plants, where rollers, drums, heat exchangers or the like must likewise frequently rotate inside a liquid bath, and therefore the problem likewise arises that the drive must not come into contact with the, possibly aggressive, liquid or may only come into contact with said liquid at certain points. The drive principle according to the invention may also be advantageously applied if a very high transmission ratio is to be realized between the drive shaft and the rotating article.

Figure 5A:
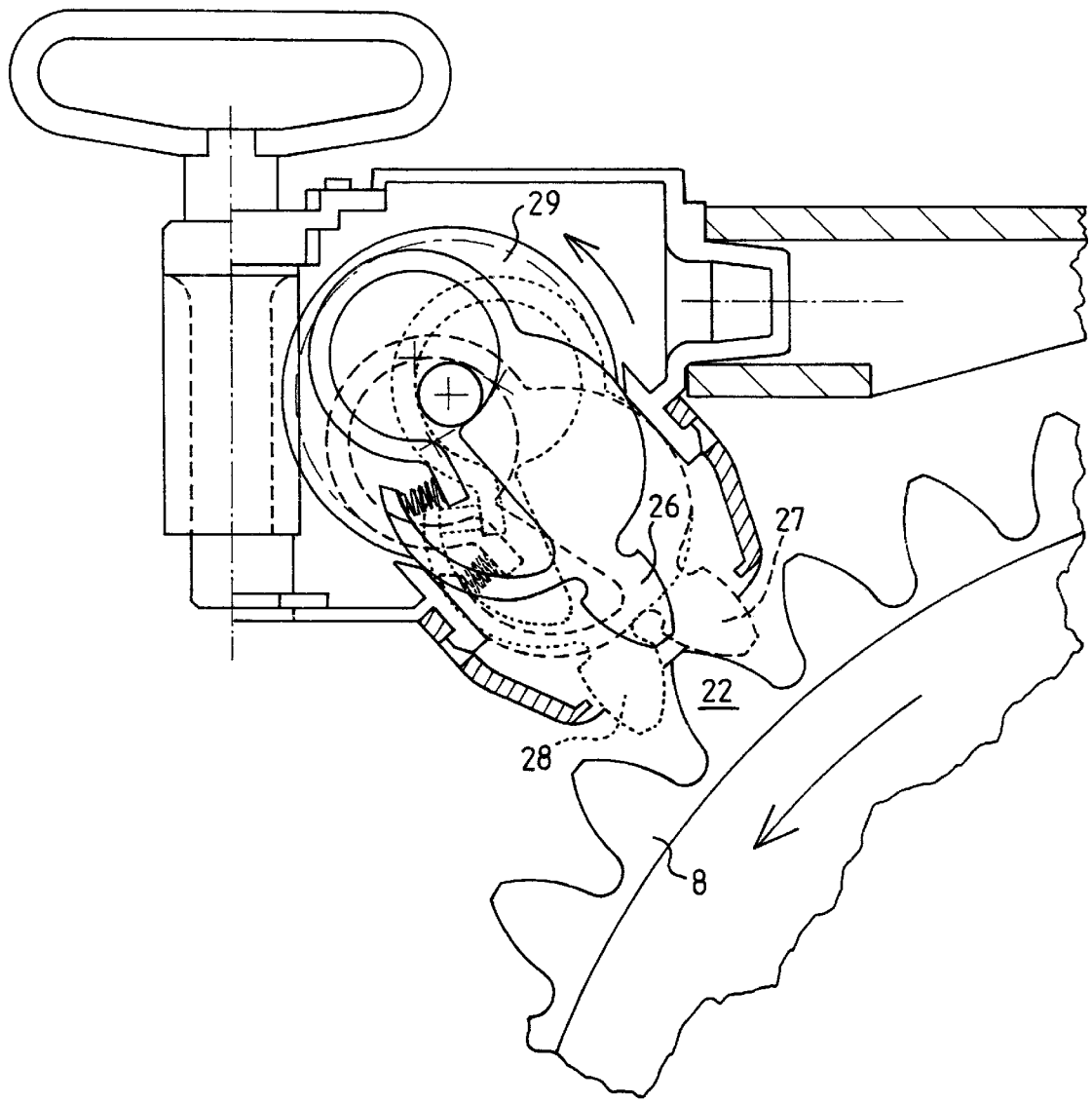
FIG. 5a shows a detail of a drive according to the invention in accordance with FIGS. 2a to e but with three drive levers for one position.
Figure 5B:
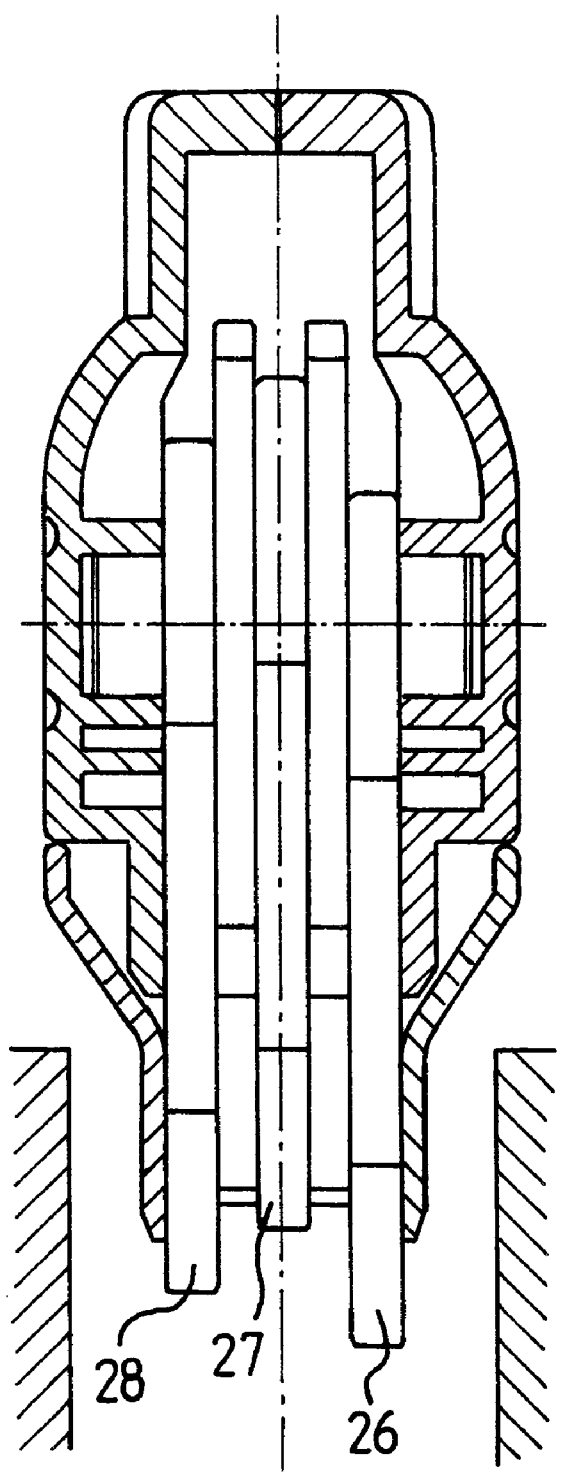
FIG. 5b shows a drive according to the invention in accordance with FIG. 5a in longitudinal section.

A variant of a drive according to the invention is shown in FIGS. 5a and b, three drive levers 26, 27, 28 being used in this drive instead of two. In a corresponding manner, drive journals are eccentrically offset on a worm wheel 29 not by 180° but by 120°. Further improved synchronism can be achieved by this embodiment, which is shown in longitudinal section in FIG. 5b to illustrate the position of the drive levers 26, 27, 28.

What is claimed is:

1. A drive for rotating an article, comprising:
a gear connectable to the rotating article in a rotationally fixed manner, said gear having a plurality of first teeth each having a first flank; an at least one movably mounted lever; and means for driving the at least one movably mounted lever, said at least one movably mounted lever having a tip that meshes with the gear and has driving contact with the gear to impart driving motion to the gear, wherein the tip forms a second tooth having a second flank, and wherein the flanks of the first teeth and the flank of the second tooth are shaped to mesh with a rolling contact there between during the driving motion.

2. The drive as claimed in claim 1, wherein during driving contact the first and second tooth flanks roll on one another essentially without radial sliding.

3. The drive as claimed in claim 2, wherein the first teeth and the second tooth are shaped according to one of involute, cycloidal, circular arc, and lantern tooth systems.

4. The drive as claimed in claim 1, wherein the means for driving comprises guide surfaces for sliding guidance of the lever.

5. The drive as claimed in claim 4, wherein the means for driving comprises an eccentric drive for the at least one lever.

6. The drive as claimed in claim 5, wherein the eccentric drive has a drive shaft for the at least one lever, and this drive shaft is arranged eccentrically on a wheel.

7. The drive as claimed in claim 6, wherein the wheel is a worm wheel, with which a worm meshes.

8. The drive as claimed in claim 7, where the worm is connected to the drive shaft of a motor via an elastic coupling.

9. The drive as claimed in claims wherein the lever is elastically mounted between the guide surfaces of the means for driving.

10. The drive as claimed in claim 9, wherein to elastically mount the at least one lever between the guide surfaces, at least part of an outer contour of the at least one lever is gripped by the guide surfaces and is elastically resilient.

11. The drive as claimed in claim 10, wherein the elastically resilient outer contour of the lever is provided by the outer contour having a narrow frame.

12. The drive as claimed in claim 11, wherein the frame is discontinuous and a spring element is fitted in place at the point of discontinuity.

13. The drive as claimed in claim 9, wherein the at least one lever has an outer contour rigidly contacting the guide surface.

14. The drive as claimed in claim 1 wherein the at least one movably mounted lever comprises at least two movably mounted levers.

15. The drive as claimed in claim 1 forming a combination with the rotating article, wherein the rotating article is one of a roller, a shaft, and a plate.

16. The drive as claimed in claim 1, wherein the at least one movably mounted lever comprises three movably mounted levers.

* * * * *